(12) United States Patent
Pugia

(10) Patent No.: US 10,976,319 B2
(45) Date of Patent: Apr. 13, 2021

(54) CELL RESPONSE ASSAY FOR CANCER AND METHODS OF PRODUCING AND USING SAME

(71) Applicant: Siemens Healthcare Diagnostics Inc., Tarrytown, NY (US)

(72) Inventor: Michael Pugia, Granger, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 85 days.

(21) Appl. No.: 16/352,684

(22) Filed: Mar. 13, 2019

(65) Prior Publication Data

US 2019/0339278 A1 Nov. 7, 2019

Related U.S. Application Data

(60) Division of application No. 15/430,445, filed on Feb. 11, 2017, now abandoned, which is a continuation of application No. 14/346,638, filed as application No. PCT/US2012/056668 on Sep. 21, 2012, now abandoned.

(60) Provisional application No. 61/538,302, filed on Sep. 23, 2011.

(51) Int. Cl.
*G01N 33/574* (2006.01)
*C12Q 1/6886* (2018.01)
*A61K 31/4745* (2006.01)

(52) U.S. Cl.
CPC ... *G01N 33/57484* (2013.01); *A61K 31/4745* (2013.01); *C12Q 1/6886* (2013.01); *G01N 33/5748* (2013.01); *G01N 33/57407* (2013.01); *G01N 33/57415* (2013.01); *G01N 33/57434* (2013.01); *C12Q 2537/143* (2013.01); *C12Q 2565/102* (2013.01); *C12Q 2600/158* (2013.01); *G01N 2333/8132* (2013.01); *G01N 2333/82* (2013.01); *G01N 2333/91205* (2013.01); *G01N 2333/96463* (2013.01); *G01N 2800/60* (2013.01)

(58) Field of Classification Search
CPC .............................................. G01N 33/57484
USPC ........................................................ 514/283
See application file for complete search history.

(56) References Cited

U.S. PATENT DOCUMENTS

| | | | |
|---|---|---|---|
| 3,772,099 | A | 11/1973 | Ryan et al. |
| 5,196,306 | A | 3/1993 | Bobrow et al. |
| 5,834,196 | A | 11/1998 | Reutelingsperger |
| 6,187,594 | B1 | 2/2001 | Kraus et al. |
| 7,179,619 | B2 | 2/2007 | Chao et al. |
| 2003/0129665 | A1 | 7/2003 | Selvan et al. |
| 2007/0026407 | A1 | 2/2007 | Matsumoto et al. |
| 2008/0038738 | A1 | 2/2008 | Weigum et al. |
| 2009/0286268 | A1 | 11/2009 | Carney et al. |

FOREIGN PATENT DOCUMENTS

| | | |
|---|---|---|
| EP | 0515194 | 10/2001 |
| WO | 2006060561 A2 | 6/2006 |
| WO | 2008048570 | 4/2008 |
| WO | 2008097552 | 8/2008 |
| WO | 2009124997 | 10/2009 |
| WO | 2009124997 A1 | 10/2009 |
| WO | 2011109440 | 9/2011 |
| WO | 2011109440 A1 | 9/2011 |

OTHER PUBLICATIONS

Tockman et al (Cancer Res., 1992, 52:2711s-2718s).*
Bebenek, Marek et al. "Fas/Fas-ligand Expressions in Primary Breast Cancer are Significant Predictors of its Skeletal Spread" Anti Cancer Research, vol. 27, pp. 215-218, 2007.
Gastl, Günther et al. "Ep-CAM overexpression in breast cancer as a predictor of survival" The Lancet, vol. 356, pp. 1981-1982; Dec. 9, 2000.
Shiozawa, Ken et al. "Reversal of Breast Cancer Resistance Protein (BCRP/ABCG2)-Mediated Drug Resistance by Novobiocin, a Coumermycin Antibiotic" Publication of the International Union Against Cancer, Int. J. Cancer, vol. 108, pp. 146-151, (2004).
Hu, Yanjie et al; "Detection of circulating tumor cells in breast cancer patients utilizing multiparameter flow cytometry and assessment of the prognosis of patients in different CTCs levels"; Cytometry Part A; 77A; pp. 213-219.
Neumeister, Veronique et al; "In Situ identification of putative cancer stem cells by multiplexing ALDH1, CD44 and Cytokeratin identifies breast cancer patients with poor prognosis"; Biomarkers, genomics, proteomics and gene regulation; The American Journal of Pathology; vol. 176; No. 5; DOI: 102353/ajpatb2010.090712; pp. 2131-2138.
Varella-Garcia, Marileila et al: "The UroVysion fluorescence in situ hybridization assay is an effective tool for monitoring recurrence of bladder cancer"; Urologic Oncology: Seminars and Original Investigations, vol. 22, No. I, Jan. 1, 2004 (Jan. 1, 2004), pp. 16-19, XP055178124, ISSN: 1078-1439, DOI: 10.1016/S1078-1439(03)00098-X * the whole document * / Jan. 1, 2004.
Liu James J. et al.: "Piwil2 is expressed in various stages of breast cancers and has the potential to be used as a novel biomarker" in IntJ Clin Exp Pathol; 2010; vol. 3; No. 4; pp. 328-337.
Wyffels 'Synthesis and preliminary evaluation of radiolabeled bis (zinc(II)-Dipicolylamine) coordination complexes as cell death imaging agents' Bioorg. Med. Chem. Jun. 1, 2011, vol. 19, pp. 3425-3433, p. 2, para 2-4.
Van Leenders, G. et al. "Demonstration of intermediate cells during human prostate epithelial differentiation in situ and in vitro using triple-staining confocal scanning microscopy" Lab Invest, 2000, vol. 80, No. 8.
PCT Search Report and Written Opinion for International Application No. PCT/US2012/056668, dated Feb. 4, 2013.

(Continued)

*Primary Examiner* — Sean E Aeder

(57) ABSTRACT

A cell response assay for cancer is provided. In the assay, the levels of a cancer cell type biomarker, a chemo resistance biomarker and a metastatic potential biomarker are simultaneously measured in a biological sample.

9 Claims, 1 Drawing Sheet

(56) References Cited

OTHER PUBLICATIONS

Cheever, et al., "The Prioritization of Cancer Antigens: A National Cancer Institute Pilot Project for the Acceleration of Translational Research", Clinical Cancer Research, Aug. 31, 2009, vol. 15, pp. 5323-5337.
Ye, et al., "Identification of Piwil2-Like (P2L) Proteins that Promote Tumorigenesis", PLoS One, Oct. 2010, vol. 5, Issue 10, pp. 1-15.
Goodman, et al., "Increased nanoparticle penetration in collagenase-treated multicellular spheroids", International Journal of Nanomedicine, 2007, vol. 2, pp. 265-274.
Gupta, et al., "Inactivation of p53 increases the cytotoxicity of camptothecin in human colon HCT116 and breast MCF-7 cancer cells", Clinical Cancer Research, Sep. 1, 1997, vol. 3, pp. 1653-1660.
Harma, et al., "Europium Nanoparticles and Time-resolved Fluorescence for Ultrasensitive Detection of Prostate-specific Antigen", Clinical Chemistry, 2001, vol. 47:3, pp. 561-568.
Herzenberg, et al. "The History and Future of the Fluorescence Activated Cell Sorter and Flow Cytometry: A View from Stanford", 2002, vol. 48:10, pp. 1819-1827.
Horan, et al., "Fluorescence Cell Labeling for in Vivo and in Vitro Cell Tracking", Methods in Cell Biology, 1990, vol. 33, Chapter 42, pp. 469-491.
Krivacic, et al., "A rare-cell detector for cancer", PNSA, Jul. 20, 2004, vol. 101, No. 29, pp. 10501-10504.
Mocellin, et al., "Circulating tumor cells: the 'leukemic phase' of solid cancers", Trends in Molecular Medicine, Mar. 2006, vol. 12, No. 3, pp. 131-139.
Wenemoser, et al., "Planarian regeneration involves distinct stem cell responses to wounds and tissue absence", Dev Biol., Aug. 15, 2010, vol. 344(2), pp. 979-991.
Pantel, et al., "Detection, clinical relevance and specific biological properties of disseminating tumour cells", Nature Reviews Cancer, May 2008, vol. 8, pp. 329-340.
Pardal, et al., "Applying the Principles of Stem-Cell Biology to Cancer", Nature Reviews Cancer, Dec. 2003, vol. 3, pp. 895-902.
Patel, at al., "Quantification of DNA Using the Luminescent Oxygen Channeling Assay", Clinical Chemistry, 2000, vol. 46:9, pp. 1471-1477.
Punnoose, et al., "Molecular Biomarker Analyses Using Circulating Tumor Cells", PLoS One, Sep. 2010, vol. 5, Issue 9, pp. 1-12.
Ullman, et al., "Luminescent oxygen channeling assay (LOCI™): sensitive, broadly applicable homogeneous immunoassay method", Clinical Chemistry, 1996, vol. 42:9, pp. 1518-1526.
Ullman, et al., "Luminescent oxygen channeling immunoassay: Measurement of particle binding kinetics by chemiluminescence", Proc. Natl. Acad. Sci., USA, Jun. 1994, vol. 91, pp. 5426-5430.
European Search Report and Opinion for EP12833913 dated Mar. 20, 2015.

\* cited by examiner

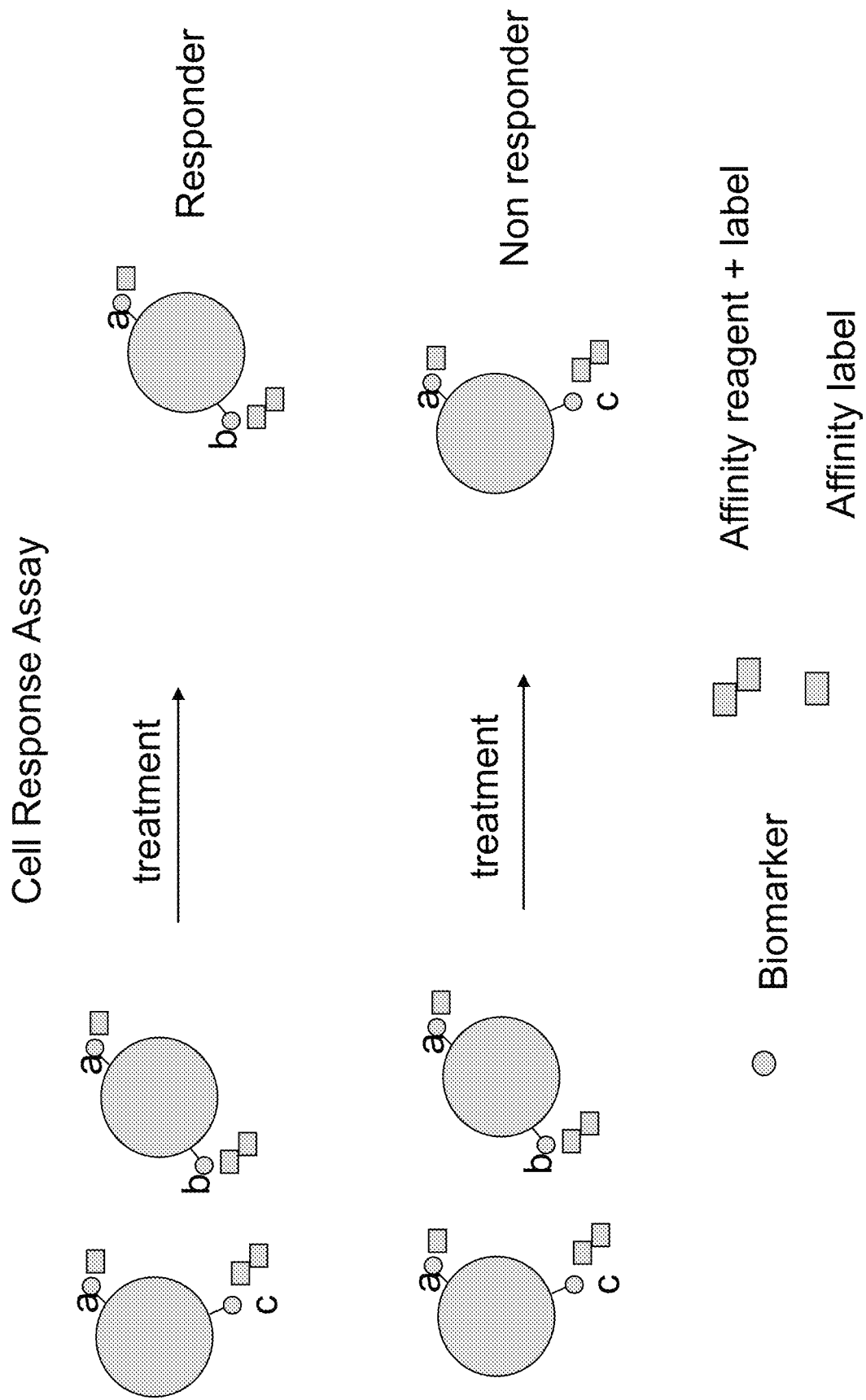

CELL RESPONSE ASSAY FOR CANCER AND METHODS OF PRODUCING AND USING SAME

CROSS REFERENCE TO RELATED APPLICATIONS/INCORPORATION BY REFERENCE STATEMENT

The present application is a divisional of U.S. Ser. No. 15/430,445, filed Feb. 11, 2017, now abandoned; which is a continuation of U.S. Ser. No. 14/346,638, filed Mar. 21, 2014, now abandoned; which is a US national stage application filed under 35 USC § 371 of international application No. PCT/US12/56668, filed Sep. 21, 2012; which claims priority to U.S. Ser. No. 61/538,302, filed Sep. 23, 2011. The entire contents of each of the above-referenced patent applications are hereby expressly incorporated by reference.

STATEMENT REGARDING FEDERALLY SPONSORED RESEARCH OR DEVELOPMENT

Not Applicable.

BACKGROUND

1. Technical Field

The presently disclosed and/or claimed inventive concept (s) generally relates to cellular assays. More particularly, but not by way of limitation, the presently disclosed and/or claimed inventive concept(s) relates to methods of assaying biological samples to determine the cellular response to treatment/therapy and/or monitor progression of a disease state.

2. Description of the Background Art

Affinity assays using fluorescence compounds are commonly used for cell and tissue analysis for biomarkers. The fluorescent compounds (labels) are attached (conjugated) to affinity molecules. Said affinity molecules may be, for example but not by way of limitation, antibodies, antigens, nucleic acid or other molecules that associate with the biomarkers of interest. This direct affinity method is a commonly used method to stain cells and tissues (See Horan and http://www.crm.ed.ac.uk/facilities/flow-cytometry/protocols/immunofluorescence-staining). The cells or tissues are incubated with conjugates, and unbound materials are washed away from cell bound materials. The conjugates are read cytometrically with a flow cytometer, scanning microscope or other device capable of detecting the fluorescence emission of the cellular material (see for example, US2008/0187198; Krivacic, 2004; and Herzenberg, 2002). Protocols vary and may or may not require cell or tissue fixation, depending on the conjugate used.

In practice, cell counts are measured using flow cytometry or scanning microscopy technologies which capture signals of cells at the excitation and emission wavelengths required to detect the dye. Different conjugates can be simultaneously determined (multiplexed) by using fluorescent dyes with distinct excitation wavelengths and emission wavelengths. Multiplexing of fluorescence signals is commonly used to detect as many properties as possible at one time. For example, biomarkers conjugated to phycoerythrin (ex 592, em 614 nm) can be measured independent from biomarkers conjugated to fluorescein-5-isothiocyanate (FITC) (ex 488, em 525 nm) using different excitation and emission filters. A list of known fluorophores is commonly available to researchers in the field (see http://www.fluorophores.org/).

Cell and tissue assays are typically performed for various types of cancer assays. Both cell and tissue assays use affinity reagents to detect biomarkers on or inside the cell, such as peptides, proteins, nucleic acid and modifications thereof (see, for example, Punnoose, 2010). Nucleic acids are measured as messenger RNA, Micro RNA and/or DNA prior to or after PCR amplification. Antibodies are also used for detecting protein biomarkers such as, but not limited to, EGFR, IGFRE, ERBB2, PSA, PL2L, kRAS, EPCAM, CK, and CD. A variety of tumor markers have detected breast, colon, prostate and melanoma cancer cells (see, for example, Mocellin, 2006). The use of biomarkers for monitoring cancer progression and/or treatment is also common practice. For example, the use of the plasminogen activator system (uPA) is monitored by measuring uPA, the plasminogen inhibitor PAI-1, and the complex of both (see Carney et al., 2009).

Cell assays are often looking for rare but clinically significant events. For example, circulating tumor cells (CTC) are significant at 5 cancer cells in 80,000,000 normal blood cells. The CTC must be isolated by enrichment or depletion to eliminate interference from normal cells (see, for example, Pantel et al., 2008). The isolated rare cells of interest then have to be assayed by methods that can detect each individual cell. Additionally the biomarkers expressed on these cells can be as low as 100 molecules per cell. Overall high sensitivity detection methods are required.

The sensitivity of traditional fluorescent labels for detecting biomarkers is generally poor for rare cell analysis. Excess affinity molecules must be used to increase the number of probes associated with the cell or tissue. This problem can be overcome partially using enzymes to catalytically increase the number of fluorescent labels. For example, Tyramide Signal Amplification (TSA) uses peroxidase enzyme to catalyze the deposition of multiple fluorophores on tyrosines of proteins by formation of tyramide with phenolic labeled fluorophores. The enzyme is associated with an affinity label to direct which cells are reacted (see, for example, Bobrow et al., 1993). However, enzymatic amplification involves multiple lengthy steps that increase the difficulty of the measurements.

Nanoparticles can be used to increase the number of fluorescent labels. However, multiple affinity molecules must also be attached to the nanoparticles, and adsorption of organic compounds onto nanoparticles also decreases the fluorescence signals. As a result, the nanoparticles with fluorescent labels (such as FITC) are no more sensitive than directly conjugated fluorescent labels. Additional problems with nanoparticles are that the size and coating must be carefully controlled for the particles to cross the cell walls (see, for example, Goodman et al., 2007).

Rare earth elements, like europium (Eu), when chelated, or in oxides or silicate lattices, have fluorescent or luminescent behaviors that allow detection thereof in a method with high sensitivity. These phosphors have been used as high sensitivity signals for detection of material. For example, Ryan et al. (1973) first explained the use of rare-earth metal activated phosphors to detect explosive material. Nanoparticles containing the europium phosphor can be fluorescent in a 500 to 700 nm range and thus can be useful as a tracer for explosives.

Chelation of europium is critical to stability and strength of the fluorescence signal. Europium has long been shown to form a strong chelate with beta diketones. Shepard and Serigne (1934) have shown thenoyltriflouracetone (TTA)

has an association constant (log Ka) of 8.0 when converted to enolate. Stary (1959) demonstrated that benzoylacetone (HBA) has a log K of 18.9. Haar and Umland (1962) showed 8-hyroxyquinoline (oxine) forms an oxinate with europium. Dyrssen (1956) describes Beta-isopropyltropolone (HIPT) log K–6.24 dissociation constant. Eu2+ resembles Ba2+ and can be complexed by various amine poly carboxylate ions such as DTPA (log Ka 23), DCTA (log Ka 19), EDTA (log Ka 17), HEDTA (log Ka 15), HTA (log Ka 11), and IMDA (log Ka 6). Matsumoto et al. (2007) demonstrated that europium with a variety of chelates in silicate nanoparticles can be a fluorophor in the range of 500 to 700 nm. Ullman et al. (1994) and Kraus et al. (2001) demonstrate europium with a variety of chelates in polystyrene nanoparticles. In particular, N,N,N',N'-{2,6-bis(3'-aminomethyl-1"-pyrazolyl)-4-phenylpyridine} tetra kis (acetic acid) (BBTA) and 3-(2-thienoyl)-1,1,1-trifluoroacetone (TTA) are useful. In general, a wide variety of compounds has been shown to complex with lanthanide elements (for example but not by way of limitation, europium (Eu)), and this complex provides stability and strength to the fluorescence signals.

In practice, rare earth metal labels (such as but not limited to, lanthanides like Eu, Sm, Tm, Pr) or others like Tb have been applied as high sensitivity fluorescents or luminescent detection technology in nanoparticles (Ullman et al. 1994; Kraus et al., 2001; and Harma et al., 2001). These labels have been applied to various analytical methods for clinical diagnostics using nanoparticles. Ullman et al. demonstrated that nanoparticles containing europium chelate were useful in diagnostics as biomarker labels that generate luminance. Kraus et al. also showed nanoparticles with Europium chelate (such as but not limited to Eu TTA3) were detectable above 500 nm and useful as diagnostic labels for biomarkers. Harma et al. showed the advantages of time resolved fluorescence using europium-label detection technology. In general europium fluorescence is either an acceptable high sensitivity label when the signal is used directly or amplified with subsequent reactions.

Another type of fluorescent label is a molecule which binds directly to the biomarker or a probe. These labels do not need affinity molecules. For example, 4',6-diamidino-2'-phenylindole, dihydrochloride (DAPI) is a probe that fluoresces blue (455 nm) when bound to double stranded DNA and excited by exposure to light at 345 nm (see, for example, Morikawa et al., 1981). The detection of DNA in cells is an indication of a living cell nucleus. Other probes containing bis(zinc2+dipicolylamine) groups bind to surfaces enriched with anionic phospholipids, especially phosphatidylserine (PS) exposed on cell membranes (see, for example, U.S. Pat. No. 7,179,616). The appearance of phosphatidylserine (PS) on the cell surface indicates cell apoptosis, prior to DNA fragmentation, morphological changes, and plasma membrane permeabilization.

Overall it is known that cell and tissue assays can be done by affinity assays whether using affinity reagents with fluorescent labels or fluorescent probes. It is also known that these signals can be multiplexed, and high sensitivity labels and probes are needed to detect rare events. Further, it is known that biomarkers can be selected for assay applications in the field of cancer.

Cell and tissues assays in the field of cancer are used to direct treatment. With the entry of more antibody-based chemotherapies, a patient's cancer must be typed to assure the cancer antigen is present (personalized medicine). The number of ever increasing cancer antigens is becoming increasingly complex (see, for example, Cheever et al., 2009). As a result, the selection of biomarkers to test is a difficult choice; the expression level, number of epitopes, expression on cancer stem cells, cellular location of expression, and the number of patients with antigen positive cancers all must be considered. Antigens with therapeutic function, immunogenicity (T cell expression), oncogenicity (association with the oncogenic process) and specificity rank highest in value. Even with a ranking, selection is not straight forward and is in need of a simplification; picking the wrong antigen for a patient is still likely, and all antigens cannot be measured at one time.

Chemo resistance is another important parameter that cell and tissue assays try to address by measuring cells and tissue during the treatment course to determine if cancer antigens are still present. Another method for determining chemo resistance is to culture or grow the cancer cells and see if the cancer antigens are expressed by living cells (see, for example, the so called EPISPOT method of Alix-anabieres et al., 2009). Another method is to measure the cancer stem cell antigens as a measure of chemo resistance (see for example, Pardal et al., 2003; and Gao et al., 2010). However, all three of these methods also rely on "picking" the right antigen and fail to give good information for all patients.

Thus the current field lacks a comprehensive measure of the metastatic potential of a cancer cell/tissue. The presently disclosed and/or claimed inventive concept(s) provide a cell based response assay that overcomes the defects and disadvantages of the prior art.

BRIEF DESCRIPTION OF THE DRAWINGS

FIG. 1 graphically depicts a cell response assay constructed in accordance with the presently disclosed and/or claimed inventive concept(s).

DETAILED DESCRIPTION

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein.

The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications and non-patent publications mentioned in the specification are indicative of the level of skill of those skilled in the art to which this presently disclosed and/or claimed inventive concept(s) pertains. All patents, published patent applications and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this presently disclosed and/or claimed inventive concept(s) have been described in terms of preferred (but non-limiting) embodiments, it will be apparent to those of skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The term "probe" as used herein will be understood to refer to any type of affinity reagent that binds to a specific biomarker as described herein. Examples of probes include, but are not limited to, antibodies (or binding fragments or derivatives thereof), receptors, organic molecules, inorganic molecules, ligands, nucleic acids (including but not limited to, DNA, RNA, microRNA, mRNA, siRNA, etc.), peptides, polypeptides, proteins, epitopes, antigens, ligands, receptors, complexes, lipids, glycoproteins, glycolipids, glycosaminoglycans, carbohydrates, polycarbohyd rates, glycoconjugates, and any combination or derivative thereof.

The term "biomarker" as used herein will be understood to refer to any target site on the surface of or inside of a cell that a probe can have affinity therefor and thus can bind to said moiety. The "biomarker" may be, for example but not by way of limitation, a nucleic acid, peptide, polypeptide, protein, epitope, antigen, ligand, receptor, complex (i.e., an MHC-peptide complex), lipid, glycoprotein, glycolipid, glycosaminoglycan, carbohydrate, polycarbohydrate, glycoconjugate, and any combination or derivative thereof.

The terms "peptide", "polypeptide" and "protein" are used herein to refer to a polymer of amino acid residues. The term "polypeptide" as used herein is a generic term to refer to native protein, protein fragments, or analogs of a polypeptide sequence. Hence, native protein, protein fragments, and analogs are species of the polypeptide genus.

The terms "polynucleotide", and "nucleic acid" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The terms "isolated nucleic acid" and "isolated polynucleotide" are used interchangeably; a nucleic acid or polynucleotide is considered "isolated" if it: (1) is not associated with all or a portion of a polynucleotide in which the "isolated polynucleotide" is found in nature, (2) is linked to a polynucleotide to which it is not linked in nature, or (3) does not occur in nature as part of a larger sequence.

The term "antibody" is used in the broadest sense, and specifically covers monoclonal antibodies (including full length monoclonal antibodies), polyclonal antibodies, multispecific antibodies (e.g., bispecific antibodies), and antibody fragments so long as they exhibit the desired biological activity. Thus, the terms "Antibody" or "antibody peptide(s)" refer to a full length immunoglobulin molecule (i.e., an intact antibody), or a binding fragment thereof that competes with the intact antibody for specific antigen binding. Binding fragments may be produced by recombinant DNA techniques, or by enzymatic or chemical cleavage of intact antibodies. Binding fragments include Fab, Fab', F(ab')2, Fv, scFv, disulfide linked Fv, Fd, diabodies, single-chain antibodies, single domain antibodies (such as but not limited to, NANOBODIES®) and other antibody fragments that retain at least a portion of the variable region of an intact antibody. See, e.g., Hudson et al. (Nature Med., 9:129-134 (2003)).

The term "antigen binding fragment" or "antigen-binding portion" of an antibody, as used herein, refers to one or more fragments of an antibody that retain the ability to bind to an antigen. The antigen-binding function of an antibody can be performed by fragments of an intact antibody. Examples of binding fragments encompassed within the term "antigen-binding fragment" of an antibody include but are not limited to, Fab, Fab', F(ab')2, Fv, scFv, disulfide linked Fv, Fd, diabodies, single-chain antibodies, single domain antibodies (such as but not limited to, NANOBODIES®), isolated CDRH3, and other antibody fragments that retain at least a portion of the variable region of an intact antibody. These antibody fragments are obtained using conventional recombinant and/or enzymatic techniques and are screened for antigen binding in the same manner as intact antibodies.

The term "epitope" includes any protein determinant capable of specific binding to an immunoglobulin or T-cell receptor. In certain embodiments, an epitope is a region of an antigen that is specifically bound by an antibody. Epitopic determinants usually include chemically active surface groupings of molecules such as amino acids, sugar side chains, phosphoryl, or sulfonyl groups. In certain embodiments, an epitope may have specific three dimensional structural characteristics (e.g., a "conformational epitope"), as well as specific charge characteristics.

The term "nanoparticle" as used herein refers to a particle having dimensions of from about 1 to about 5000 nanometers, and having any size, shape or morphology. The nanoparticles utilized in accordance with the presently disclosed and/or claimed inventive concept(s) may be naturally occurring, commercially available nanoparticles, or the nanoparticles may be synthesized for use in accordance with the presently disclosed and/or claimed inventive concept(s), as described herein below and as known in the art. Particular examples of nanoparticles that may be utilized in accordance with the presently disclosed and/or claimed inventive concept(s) include, but are not limited to, poly(lactic-co-glycolic) acid (PLGA) nanoparticles, poly lactic acid (PLA) nanoparticles, Chitosen nanoparticles, liposomes, and derivatives or combinations thereof.

As used herein, the terms "label" or "labeled" refers to incorporation of a detectable marker, e.g., by attachment of a fluorescent, enzymatic or colorimetric label or incorporation of a radiolabeled amino acid. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The terms "label", "detectable marker" and "detection moiety" are used interchangeably herein.

A fluorophore may be employed in the methods of the presently disclosed and/or claimed inventive concept(s) and detected via any of numerous colorimetric and fluorescence detection methods. Depending on the application and purpose, such methods include, but are not limited to, absorbance spectroscopy, fluorescence spectroscopy, fluorescence activated cytometry (FACS), fluorescence microscopy, fluorescence resonance energy transfer (FRET), and the like.

Various types of fluorophores, depending on the application and purpose, may be employed in accordance with the presently disclosed and/or claimed inventive concept(s). Examples of suitable fluorophores are described herein below. Examples of suitable fluorophores are described herein below. Other examples are given in U.S. Pat. Nos. 7,465,747 and 7,955,859, issued to Matsumoto et al. on Dec. 16, 2008 and Jun. 7, 2011, respectively; and US Publication No. US2007/0026407, published Feb. 1, 2007 (the entire contents of which are expressly incorporated herein by reference in their entirety).

Ample guidance regarding fluorophore selection, methods of linking fluorophores to various types of molecules, and methods of use thereof is available in the literature of the art [for example, refer to: Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Therefore, no further description is considered necessary.

The terms "substantial increase" and "substantial decrease", as well as grammatical equivalents thereof, will be understood herein to refer to at least a 12% increase or decrease, such as at least a 30% increase or decrease, at least a 50% increase or decrease, at least a 75% increase or decrease, or at least a 90% increase or decrease.

The terms "cancer" and "cancerous" refer to or describe the physiological condition in mammals that is typically characterized by unregulated cell growth. Examples of cancer include but are not limited to, carcinoma, lymphoma, blastoma, and sarcoma. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "metastasis" as used herein will be understood to refer to the spread of cancer from a primary tumor to other parts of the body. Metastasis is a sequential, multistep process in which tumor cells detach from a primary tumor, migrate through the basement membrane and extracellular matrix, and invade the lymphatic and/or blood systems. This is followed by the establishment of secondary tumors at distant sites.

"Mammal" for purposes of treatment refers to any animal classified as a mammal, including human, domestic and farm animals, nonhuman primates, and zoo, sports, or pet animals, such as dogs, horses, cats, cows, etc.

The term "patient" includes human and veterinary subjects. In certain embodiments, a patient is a mammal. In certain other embodiments, the patient is a human.

The term "biological sample" as used herein will be understood to refer to a sample of biological fluid. Biological samples include, but are not limited to, blood, plasma, serum, sputum, cerebrospinal fluid (CSF), tears, mucus, urine, tissue, other types of specimens, and the like.

The phrase "providing a biological sample" as used herein refers to obtaining a biological sample for use in methods described and claimed herein. Most often, this will be done by removing a sample of cells from an animal, but can also be accomplished by using previously isolated cells (e.g., isolated by another person, at another time and/or for another purpose). The step of "providing a biological sample" may further include various isolation and/or purification steps known in the art for providing a specific component of a biological sample for use in the methods described and claimed herein.

Numerous aspects and advantages of the inventive concept(s) will be apparent to those skilled in the art upon consideration of the following detailed description which provides illumination of the practice of the presently disclosed and/or claimed inventive concept(s).

The presently disclosed and/or claimed inventive concept(s) generally relates to multiplexed direct affinity conjugate assays of cells using probes able to determine a cellular response to treatments; this type of assay is herein termed a "cell response assay".

The presently disclosed and/or claimed inventive concept(s) generally relates to the use of a combination of biomarkers for cancer cell/tissue type, metastatic potential and chemo resistance in a multiplexed affinity assay for cancer cells and tissue. Fluorescent labels either conjugated to affinity molecules/reagents or capable of directly binding to the biomarker are used and are referred to herein as labeled probes. This combination of labeled probes for biomarkers allows determination of the cellular response to treatments by simultaneously measuring cell type, chemo resistance nature, and metastatic potential and/or cell viability, and allows simple multiplexed signals with high sensitivity.

Surprisingly, the biomarker affinity markers selected in this order solves the problem of "picking" the right antigen for cancer antigen type and also provides accurate information on the response to therapy. More particularly, the presently disclosed and/or claimed inventive concept(s) relates to methods of using said affinity molecules and molecular probes as compositions, dosage forms, and kits.

The presently disclosed and/or claimed inventive concept(s) combines cell biomarker(s) for tissue type with biomarker(s) for metastatic potential and biomarker(s) for cell viability in an affinity assay for cancer cells and tissue. In FIG. 1, the biomarker for cancer cell type is represented as biomarker A and is always present in the disease state. The biomarker for metastatic potential is represented as biomarker B and is present in the disease state with metastatic invasiveness potential. The biomarker for chemo resistance is represented as biomarker C and is present in unresponsive cells. Fluorescent labels either conjugated to the affinity reagents or capable of directly binding the biomarker are used to simultaneously detect biomarkers A, B and C; simultaneous detection is obtained by using fluorescent labels that are detectable at different excitations and/or emission wavelengths.

The desired response to the treatment would be first for the number of cancer cells to decrease overall. However, the unexpected response identified by the presently disclosed and/or claimed inventive concept(s) is for biomarker B (i.e., metastatic potential) to increase or become present in the course of treatment in a greater proportion of cancer cells detected by biomarker A, and for biomarker C (i.e. chemo resistance) to decrease or become absent in the course of treatment in a greater proportion of cancer cells detected by biomarker A. In order for this combination of cell biomarkers to correctly predict the response, the biomarker for tissue type, metastatic potential and cell viability must be biochemically linked in a process. Biomarkers A, B and C must co-exist in the disease state and be fundamental to progression or relapse of the disease. Further, the presence of biomarkers B and C must be linked such that the presence of one facilitates the absence of the other. This combination of biomarkers allows the determination of the cell response to treatments; by simultaneously measuring cell type, chemo resistance nature, and metastatic potential (and possibly also cell viability), the "cell based response assay" can accurately monitor cancer treatment and/or monitor disease progression/relapse.

Turning now to the particular embodiments of the presently disclosed and/or claimed inventive concept(s), one embodiment thereof is directed to a multiplexed assay for cancer. Said assay involves simultaneously measuring: (1) at least one cancer cell type biomarker (also referred to herein as Biomarker A) in a biological sample of a cancer patient utilizing a first labeled probe that binds to said cancer cell type biomarker; (2) at least one chemo resistance biomarker (also referred to herein as Biomarker C) in the biological sample utilizing a second labeled probe that binds to said chemo resistance biomarker; and (3) at least one metastatic potential biomarker (also referred to herein as Biomarker B) in the biological sample utilizing a third labeled probe that binds to said metastatic potential biomarker. The at least three labeled probes are measured at different excitations and emission wavelengths.

The assays/methods described herein may be utilized for a specific cancer, or the assays/methods may be general assays for all types of cancers. Likewise, the cancer cell type biomarker utilized in accordance with the presently disclosed and/or claimed inventive concept(s) may be a non-specific cancer cell biomarker, or may be specific for a certain type of cancer. Examples of cancers that may be detected/monitored by the currently disclosed and/or claimed inventive concept(s) include, but are not limited to, lung, bronchus, colon, rectum, pancreas, prostate, breast, liver, bile duct, bladder, ovary, brain, central nervous system (CNS), kidney, pelvis, uterine corpus, oral cavity or pharynx or melanoma cancers.

Non-limiting examples of non-specific cancer cell type biomarkers include, but are not limited to, cytokeratins (CK), EpCAM, N-cadherin, E-cadherin and vimentin.

For example but not by way of limitation, the carcinoma cells may be indicated by cytokeratin (CK) as a biomarker A, and the first labeled probe may comprise multiple labeled antibodies for separate cytokeratins (such as but not limited to, cytokeratins 8/18/19. Cytokeratins (CK) are proteins of keratin-containing intermediate filaments found in the intracytoplasmic cytoskeleton of epithelial tissue and refer to a family of fibrous structural proteins. There are two fundamental types of cytokeratins: the acidic type I cytokeratins and the basic or neutral type II cytokeratins. Cytokeratins are usually found in pairs comprising a type I cytokeratin and a type II cytokeratin. Basic or neutral cytokeratins include (but are not limited to) CK1, CK2, CK3, CK4, CK5, CK6, CK7, CK8 and CK9. Acidic cytokeratins include (but are not limited to) CK10, CK12, CK 13, CK14, CK16, CK17, CK18, CK19 and CK20.

In other instances the, Epithelial cell adhesion molecule (EpCAM) is a protein that signifies the presence of epithelial cells in a carcinoma. EpCAM has also been designated as TACSTD1 (tumor-associated calcium signal transducer 1) and CD326 (cluster of differentiation 326). Thus, the terms "EpCAM", "TACSTD1" and "CD326" are used herein interchangeably.

In other instances, some cancer cells undergo an Epithelial to Mesenchymal transition (EMT) that may be indicated by an increase in cancer cell biomarkers such as but not limited to, Vimentin and Galectin-3, which signify cells with a loss of anchorage. Alternatively, certain other cancer cells undergo a Mesenchymal to Epithelial transition (MET) indicated by an increase in cancer cell biomarkers such as but not limited to, N-Cadherin, and E-Cadherin. The EMT and MET stages for cancer cells signify a change in sub type of cells. It is important to detect as many cancer cells as possible and to additionally know their sub types to measure the entire tumorigenicity.

The term "cancer cell type biomarker" also includes markers that identify specific genetic mutations that cause oncoproteins or oncogenes to be regulated (whether tumor promoting or tumor suppressing). These types of cancer cell type biomarkers may be utilized alone or in combination with any of the other cancer cell type biomarkers described herein above. Examples of these types of cancer cell type biomarkers include, but are not limited to, HER2/neu, VEGF-165, KRAS, EGFr, WAF, BAX-1, PDGF, Rb, Jagged 1, Notch, VEGF, VEGHR, k-Ras, CAIX, MIB1, MDM, PR, ER, SEL5, SEM1, PI3K, Akt2, twist 1, EML-4, ALK, Braf, DRAFF, c-met, and combinations thereof. These oncoproteins and oncogenes are used to direct targeted therapies based on their presence in/on cells. For example, the presence of HER2/neu is used to prescribe Herceptin therapy; however, HER2/neu, as with other oncoprotein/oncogene markers, is often only expressed on a fraction of cancer cells, and not all patients have the specific genetic mutation leading to the biomarker. HER2/neu-positive expression is present in only 10-20% of breast cancer patients, and even in the HER2/neu-positive patients, the marker is only present in approximately 30% of their circulating tumor cells. Therefore these markers are often measured in combination with another cancer cell type biomarker.

In other instances, the carcinoma cells may be indicated by a tissue specific marker. For example, Prostate-Specific Antigen (PSA) is a protein that signifies the presence of cells of the prostate gland. Non-limiting examples of specific cancer cell type biomarkers include, but are not limited to: prostate specific antigen (PSA) or prostate specific membrane antigen (PSMA) can be used to detect prostate cancer cells; MUC1, CA 15-3 and CA 27-29 can be used to detect breast cancer cells; Carcinoembryonic Antigen (CEA), CA19-9 or Galactosyl Transferase II can be used to detect colon cancer cells; MSLN (mesothelin) can be used to detect pancreatic cancer cells; CA 125 or Follicle-Stimulating Hormone (FSH) receptor can be used to detect ovarian cancer cells; Alpha-Fetoprotein can be used to detect liver cancer cells; Melan-A (MLANA), Tyrosinase (TYR), CSPG4, or MITF can be used to detect melanoma cancer cells; and Parathyoid related protein (PTHP) or TSHR can be used to detect thyroid cancer cells.

Any metastatic potential biomarkers known in the art or otherwise contemplated herein may be utilized in accordance with the presently disclosed and/or claimed inventive concept(s). The third labeled probe may be any probe capable of detecting said metastatic potential biomarker; for example but not by way of limitation, the third labeled probe may be one or more labeled antibodies against any of the markers of tumor cell invasiveness listed below. In some instances, the metastatic potential biomarker may be measured as a ratio of one of the below-listed biomarkers to the cancer cell type biomarker. Particular non-limiting examples of biomarkers of metastatic potential that may be utilized in accordance with the presently disclosed and/or claimed inventive concept(s) include a marker(s) of tumor cell invasiveness where the marker measures cancer cell invasion into the extracellular membrane through proteolytic events, such as urokinase plasminogen activator (uPA), plasminogen activator inhibitor (PAI-1), CD95, serine proteases such as plasmin, ADAM, and others; serine protease inhibitors such as Bikunin; matrix metalloproteinases such as MMP9; matrix metalloproteinase inhibitors such a TIMP-1; and combinations thereof. For example but not by way of limitation, a prostate cancer assay may measure PSA as a cancer cell type biomarker, and measure a ratio of PAI-1/PSA for metastatic potential.

Any chemo resistance biomarkers known in the art or otherwise contemplated herein may be utilized in accordance with the presently disclosed and/or claimed inventive concept(s). In certain embodiments, the chemo resistance biomarker is a biomarker that detects the prevention of cell death (apoptosis), for example but not by way of limitation, a detection of the presence of a cancer stem cell biomarker, such as but not limited to, PL2L piwi like, ADLH, β-integrin, α6 integrin, c-kit, c-met, LIF-R, CXCR4, ESA, CD 20, CD44, CD133, CK5, TRAF2 and ABC transporters. In another non-limiting example, cancer cells that contain CD44 but lack CD24 are indicative of a cancer stem cell phenotype. Also, cancer cells that lack CD45 and CD31 but contain CD34 are indicative of a cancer stem cell. Also, cancer cells that contain CD44 and CD24 as well as ESA are indicative of a cancer stem cell. Further, the presence of both CD24 and ESA are indicative of a cancer stem cell. Somatic stem cells in solid tumor carcinomas can become cancer stem cells. Other cancer cells resistant to CD95 induced-apoptosis are chemo resistant. Cancer stem cells are chemo resistant in nature, and contain a capacity for self renewal (asymmetric divisions) as well as being capable of differentiation into a hierarchy of progeny cells to form a tumor. Cancer stem cell self renewal is activated by the stem cell signaling pathways (Wnt, Sonic Hedge hog and Notch) and at the epigenetic level by Polycomb gener (BMI-1 and EZH2). This self renewal occurs at the expense of apoptosis signaling pathways (Caspase 3, 5, 8, p53). Measuring cancer stem cell biomarkers and combinations thereof as an indication of chemo resistance provides a measure of (a) drug resistance, (b) the inability to activate apoptosis, and/or (c) the inability to shutdown self renewal.

The probes described and claimed herein may be labeled by any methods known in the art or otherwise contemplated herein. For example, but not by way of limitation, the labels of the first, second and third (and any additional fourth, fifth, sixth, etc.) labeled probes may be selected from a comprehensive catalogue of fluorescent (luminescent) dyes. For example but not by way of limitation, a comprehensive catalogue exists online at http://www.fluorophores.org (the entire contents of which are expressly incorporated herein by reference). This catalogue includes commonly used labels such as fluorescein-5-isothiocyanate (FITC), phycoerythrin, sulforhodamine 101 (Texas Red), 2-[4-(aminoiminomethyl)phenyl]-1H-Indole-6-carboximidamide (DAPI), 3H-Indolium (Cy5), 1H-benz[e]indolium (Cy 5.5), 3H-Indolium (Cy 7), ALEXA FLUOR® 488, ALEXA FLUOR® 555, ALEXA FLUOR® 647, and combinations and derivatives thereof that have been synthesized in order to provide better reagents. Additionally, rare earth metals and rare earth element-containing nanoparticles can be used as labels.

The biological samples utilized in the methods of the presently disclosed and/or claimed inventive concept(s) may be utilized in the form they are obtained (i.e., tissue sample), or they may be exposed to one or more isolating steps (i.e., isolation of cancer cells therefrom).

While the assays described herein above describe the measurement of three biomarkers with three labeled probes, it is to be understood that one or more additional biomarker(s) may also be measured in the assay (utilizing additional one or more additional labeled probe(s)). For example, but not by way of limitation, the assay may further include measuring at least one additional biomarker in the biological sample utilizing a fourth labeled probe that binds to said additional biomarker, measuring a second additional biomarker in the biological sample utilizing a fifth labeled probe that binds to said additional biomarker, measuring a third additional biomarker in the biological sample utilizing a sixth labeled probe that binds to said additional biomarker, etc. Ideally, a maximum of six to eight labeled probes are utilized; otherwise, it is difficult to detect all of the labeled probes at different, non-overlapping excitations and emission wavelengths.

These additional biomarkers may include biomarkers that detect other cellular properties, specifically the presence of cell nuclei or of intact cell membranes, for the cells that are positive for the cancer cell type biomarker. For example but not by way of limitation, the presence of cell nuclei may be detected utilizing a DNA binding probe such as but not limited to, DAPI. In another non-limiting example, the detection of intact cell membranes may involve the detection of anionic phospholipids (such as but not limited to, phosphatidylserine) on the surface of cells, and the second labeled probe may be bis(zinc2+dipicolylamine) and/or PSVue™.

The one or more additional biomarker(s)/labeled probe(s) may also be utilized to reduce any false positive results obtained with the cancer cell type biomarker; for example but not by way of limitation, white blood cells may be excluded from the assay by excluding cells positive for one or more markers of cluster of differentiation (also referred to as "cluster of designation"; often abbreviated as CD). For example but not by way of limitation, markers such as CD45, CTLA-4, CD4, CD68 and/or CD8 present on white blood cells can be used to indicate that a cell is not a cancer cell. In a particular non-limiting example, CD45 antigen (also known as PTPRC, Protein tyrosine phosphatase receptor type C, and originally called leukocyte common antigen (all terms used herein interchangeably)) is useful in detecting all white blood cells. Additionally, CD45 can be used to differentiate the different types of white blood cells when combined with other CD markers. For example, granulocytes are indicated by CD45+, CD15+; monocytes are indicated by CD45+, CD14+; T lymphocytes are indicated by CD45+, CD3+; T helper cells are indicated by CD45+, CD3+, CD4+; cytotoxic T cells are indicated by CD45+, CD3+, CD8+; B lymphocytes are indicated by CD45+, CD19+ or CD45+, CD20+; thrombocytes are indicated by CD45+, CD61+; and natural killer cells are indicated by CD16+, CD56+, CD3−. Additionally, two commonly used CD molecules are CD4 and CD8, which are, in general, used as markers for helper and cytotoxic T cells, respectively. These molecules are defined in combination with CD3+, as some other leukocytes also express these CD molecules (some macrophages express low levels of CD4; dendritic cells express high levels of CD8).

The presently disclosed and/or claimed inventive concept(s) is also directed to a kit that includes the first, second and third labeled probes (that bind to a cancer cell type biomarker, a chemo resistance biomarker, and a metastatic potential biomarker, respectively) as described in detail herein above. Additional labeled probes for detecting other biomarkers as further described herein above may also be included in the kit. All of the labeled probes present in the kit are measured at different excitations and emission wavelengths.

The kit may also include means for isolating cancer cells from a biological sample. Said means are well known in the art (see for example, Lianidou and Markou, 2011; the entire contents of which are hereby expressly incorporated herein by reference); therefore, no additional discussion thereof is deemed necessary.

The presently disclosed and/or claimed inventive concept(s) is also directed to methods of (1) monitoring cancer treatment in a cancer patient undergoing said treatment, and (2) monitoring progression/relapse of the disease in the cancer patient. In the method of (1) monitoring cancer treatment, a first biological sample is obtained from the patient prior to exposure to a cancer treatment, and a second biological sample is obtained from the patient following exposure to the cancer treatment. In the method of (2) monitoring progression/relapse of disease, the first biological sample is obtained from the patient at a first time point, and the second biological sample is obtained from the patient at a subsequent time point. In both methods, the levels of a cancer cell type biomarker (as described herein above), a chemo resistance biomarker (as described herein above), and a metastatic potential biomarker (as described herein above) are then measured utilizing first, second and third labeled probes, respectively (as described in detail herein above), in the first and second biological samples. The cells to which the first labeled probe is bound are identified in the first and second biological samples, and then the levels of (i) the chemo resistance biomarker and (ii) the metastatic potential marker in the cells to which the first labeled probe is bound are compared in the first and second biological samples. It is then determined in the method of (1) that the cancer treatment is effective if the level of the chemo resistance biomarker is decreased and the level of the metastatic potential biomarker is increased in the second biological sample when compared to the first biological sample; alternatively, it is then determined in the method of (2) that the cancer has progressed/relapsed if the level of the chemo resistance biomarker is increased and the level of the metastatic potential biomarker has decreased in the second biological sample when compared to the first biological sample.

The biological samples utilized in the methods of the presently disclosed and/or claimed inventive concept(s) may be utilized in the form they are obtained (i.e., tissue sample), or they may be exposed to one or more isolating steps (i.e., isolation of cancer cells therefrom).

While the methods described herein above describe the measurement of three biomarkers with three labeled probes, it is to be understood that additional biomarkers may also be included in the methods (utilizing additional labeled probes). For example, but not by way of limitation, the method may further include measuring at least one additional biomarker in the first and second biological samples utilizing a fourth labeled probe that binds to said additional biomarker, measuring a second additional biomarker in the first and second biological samples utilizing a fifth labeled probe that binds to said additional biomarker, measuring a third additional biomarker in the first and second biological samples utilizing a sixth labeled probe that binds to said additional biomarker, etc. Ideally, a maximum of six to eight labeled probes are utilized; otherwise, it is difficult to detect all of the labeled probes at different, non-overlapping excitations and emission wavelengths. When additional biomarkers are measured, the methods may also include the step of comparing the levels of the additional biomarker(s) in the cells to which the first labeled probe is bound in the first and second biological samples.

These additional biomarkers may include biomarkers that detect other cellular properties, specifically the presence of cell nuclei or of intact cell membranes, for the cells that are positive for the cancer cell type biomarker. For example but not by way of limitation, the presence of cell nuclei may be detected utilizing a DNA binding probe such as but not limited to, DAPI. In another non-limiting example, the detection of intact cell membranes may involve the detection of anionic phospholipids (such as but not limited to, phosphatidylserine) on the surface of cells, and the second labeled probe may be bis(zinc2+dipicolylamine) and/or PSVue™.

The one or more additional biomarker(s)/labeled probe(s) may also be utilized to reduce any false positive results obtained with the cancer cell type biomarker; for example but not by way of limitation, white blood cells may be excluded from the methods by excluding cells positive for one or more markers of cluster of differentiation (as described in detail herein above).

EXAMPLES

Examples are provided hereinbelow. However, the presently disclosed and/or claimed inventive concept(s) is to be understood to not be limited in its application to the specific experimentation, results and laboratory procedures. Rather, the Examples are simply provided as one of various embodiments and are meant to be exemplary, not exhaustive.

Example 1

Multiplexed Assay for Breast Cancer

The following procedure shows the multiplexing of Biomarkers A (cancer cell type), B (metastatic potential) and C (chemo resistance) using a unique combination of affinity reagents with fluorescent labels and an affinity label to provide a multiplexed assay for breast cancer. This allows the simultaneous measurement of cancer cell type, chemo resistance nature, and metastatic potential, as described herein above, in combination with a marker indicating the presence of cell nucleus (utilizing a nucleic acid binding probe). The data demonstrated that four simultaneous signals can be measured with this combination but not with the traditional combinations of the prior art. The presently disclosed and/or claimed inventive concept(s) has the potential to measure up to eight signals utilizing various fluorophores taught herein.

The procedure to test the method was to collect 4 mL normal whole blood fresh into a VACUTAINER® tube (BD 6 mL VACUTAINER® K2EDTA tube, 10.8 mg, ref 367863, Becton Dickinson, Oakville, ON) and transfer the blood into a round centrifuge tube sealed with top. Cancer cells were added by 40 µL of breast cell cancer suspension to obtain a range of 3000 to 8000 cells/mL (8 cells/4 or 1-2 per high powered filed HRP (HRP=0.2 µL)). The blood was lysed by adding 3 mL of lysis buffer (155 mM $NH_4Cl$, 20 mM $KHCO_3$, 0.1 mM $Na_2EDTA$, pH 7.4). The tubes were rolled tubes to assure that the cells were evenly distributed and that lysis was complete, and then the sample was spun down for 15 minutes at 12,000 rpm. Next, the plasma was decanted as waste supernatant, and 4.0 mL of TES buffer (50 mM N-Tris [Hydroxymethyl]-2-aminoethane-sulfonic acid: TES, pH 7.4, 2150 mM NaCl, 2 mM $MgSO_4$ and 1 mM $KCO_3$) and 1% albumin was added, and the tube was rocked to mix the cells. The tube was spun down again for 15 minutes at 12,000 rpm, and the supernatant was decanted as waste. A final 2.0 mL of TES wash buffer was added with rocking to mix cells.

The cells were then reacted with the reagents by taking 0.5 mL of washed blood to the centrifuge tube, and 40 µL of antibodies for HER2/neu labeled with Cy5 and 40 µL of antibodies for urokinase like plasminogen activator (uPA) or plasminogen activator inhibitor (PAI-1) labeled with Texas Red (at working stock of 0.001 to 0.1 mg/mL) and PL2L piwi like labeled with FITC (at working stock of 0.001 to 0.1 mg/mL) were added. Next, 10 µl of a 100 µg/ml 4,6 Diamidino-2-phenylindole dihydrochloride (DAPI; a nucleic acid binding probe) was added from a solution in TES buffer. This was followed by incubation for 15 minutes at 37° C.

The sample was centrifuged down for 5 minutes @ 7500 rpm, and the supernatant was decanted off as waste (~450 µL). 500 µL of TES buffer was then added, and the sample was vortexed and centrifuged down at 5 minutes @ 7500 rpm. Again, the supernatant was decanted off by tapping as waste (~450 µL). A final 500 µL of TES wash buffer was added for final imaging, and 5 µL of the solution was placed on a slide with a long cover slip of glass. Phase contrast and fluorescence microscopy was conducted with the Leica DM5000 (Leica Microsystems, Buffalo Grove, Ill.). A sample of cells was stained with the PSS-550 probe (ex 553, em 615 nm) and measured with an excitation band pass filter at 540-580 nm and an emission band pass filter at 610-680 nm to determine cell membrane flopping as a measure of cell death in addition to cell counts.

The Texas Red label (ex 592, em 614 nm) was measured with an excitation band pass filter at 540-580 nm and an emission band pass filter at 610-680 nm. The FITC label (ex 488, em 525 nm) was measured with an excitation band pass filter at 460-500 nm and an emission band pass filter at 512-543 nm. The DAPI probe (ex 355, em 460 nm) was measured with an excitation band pass filter at 340-380 nm and an emission band pass filter at 450-490 nm. The Cy5 label (ex 646, em 676 nm) was measured with an excitation band pass filter at 590-650 nm and an emission band pass filter at 665-735 nm.

The ideal multiplexing was demonstrated by combination of the rare earth nanoparticles with FITC, Texas Red, Cy5 and DAPI. The europium nanoparticle (ex 355, em 617 nm) was measured at an excitation filter band pass at 340-380 nm and emission long pass filter of >590 nm. Simultaneously measuring biomarkers for cancer cell type, metastatic potential and chemoresistance, along with a biomarker indicating the presence of cell nucleus was possible, along with the removal of false positives (i.e., white blood cells) by detecting the presence of the biomarker CD45. Current data allows for five signals. However, the assays/methods described and claimed herein have the potential for detection and measurement of six signals/biomarkers, if the rare earth nanoparticles can be multiplexed into three different emission signals. The europium label greatly increased signal over FITC and Texas Red by 2-3 orders of magnitude.

Example 2

Cell Response Assay for Breast Cancer

A novel cell response assay for breast cancer was developed by using HER2/neu as a tissue type marker for carcinoma breast cancer (Biomarker A) that is always present in the disease state. Biomarker B for metastatic potential utilized uPA and PAI antigen; these are markers of tumor invasiveness and are present in aggressive cancer cell differentiation and growth and increase with metastatic invasiveness potential of the cells. Biomarker C for chemo resistance utilized PL2L piwi like antigen (see for example, Gao et al., 2008).

The procedure shown in Example 1 was used to measure cancer cells before and after treatment with and without camptothecin. Camptothecin is known to activate apoptosis in cancer cells and kill cancer cells like a chemotherapy agent (See Gupta, 1997). Cells were tested by the cell response assay and by a traditional prior art assay. The novel "cell response assay" utilized HER2/neu as Biomarker A for cell type, the tumor invasiveness markers uPA & PAI-1 as Biomarker B for metastatic potential, and the cancer stem cell marker PL2L piwi like as Biomarker C for chemo resistance nature. The traditional assay used EpCAM as a marker for epithelial tissue type and cytokeratin (CK) as a marker of cells of cancer origin. Additionally, CD45, a marker for white blood cells, was used to reduce false results, with CD45 positive results being excluded from the analysis. Both the traditional and cell response assays used DAPI to determine the presence of cell nuclei.

The camptothecin concentration could be adjusted to be sufficient to kill >80%, 60% and 40% of the cancer cells in cultures. Cellular analysis showed cancer cell count to decrease as the cell death % increased and phosphatidylserine flopping increased. Cellular analysis showed biomarker B, namely uPA and PA1, to increase (or was detected in a greater number of cancer cells) when the cell death % was highest. Cellular analysis showed biomarker C, namely PL2L piwi like to decrease (or was detected in a lesser number of cancer cells) when the cell death % was highest. All three biomarkers co-exist in the disease state and were fundamental to progression or relapse of the disease. This analysis of the specific combination of biomarkers described and claimed herein allows the determination of the cellular response to treatments by simultaneously measuring cancer cell type, chemo resistance nature, and metastatic potential (with or without the additional measurement of cell viability), and is herein termed a "cell based response assay".

In contrast, in the traditional assay, the CD45 biomarker does not co-exist with EpCAM and CK. Both EpCAM and CK were present in all cells independent of the % of cells that were killed.

Example 3

Multiplexed Assay for Prostate Cancer

The following procedure shows the multiplexing of Biomarkers A (cancer cell type), B (metastatic potential) and C (chemo resistance) using a unique combination of affinity reagents with fluorescent labels and an affinity label to provide a multiplexed assay for prostate cancer. This allows the simultaneous measurement of cancer cell type, chemo resistance nature, and metastatic potential, as described herein above, in combination with a marker indicating the presence of cell nucleus (utilizing a nucleic acid binding probe). The data demonstrated that four simultaneous signals can be measured with this combination but not with the traditional combinations of the prior art. The presently disclosed and/or claimed inventive concept(s) has the potential to measure up to eight signals utilizing various fluorophores taught herein.

The procedure to test the method was to collect 4 mL normal whole blood fresh into a VACUTAINER® tube (BD 6 mL VACUTAINER® K2EDTA tube, 10.8 mg, ref 367863, Becton Dickinson, Oakville, ON) and transfer the blood into a round centrifuge tube sealed with top. Cancer cells were added by 40 µL of prostate cell cancer suspension to obtain a range of 3000 to 8000 cells/mL (8 cells/µL or 1-2 per high powered filed HRP (HRP=0.2 µL)). The blood was lysed by adding 3 mL of lysis buffer (155 mM $NH_4Cl$, 20 mM $KHCO_3$, 0.1 mM $Na_2EDTA$, pH 7.4). The tubes were rolled tubes to assure that the cells were evenly distributed and that lysis was complete, and then the sample was spun down for 15 minutes at 12,000 rpm. Next, the plasma was decanted as waste supernatant, and 4.0 mL of TES buffer (50 mM N-Tris [Hydroxymethyl]-2-aminoethane-sulfonic acid: TES, pH 7.4, 2150 mM NaCl, 2 mM $MgSO_4$ and 1 mM $KCO_3$) and 1% albumin was added, and the tube was rocked to mix the cells. The tube was spun down again for 15 minutes at 12,000 rpm, and the supernatant was decanted as waste. A final 2.0 mL of TES wash buffer was added with rocking to mix cells.

The cells were then reacted with the reagents by taking 0.5 mL of washed blood to the centrifuge tube, and 40 µL of antibodies for PSA labeled with Cy5 and 40 µL of antibodies for urokinase like plasminogen activator (uPA) or plasminogen activator inhibitor (PAI-1) labeled with Texas Red (at working stock of 0.001 to 0.1 mg/mL) and PL2L piwi like labeled with FITC (at working stock of 0.001 to 0.1 mg/mL) were added. Next, 10 µl of a 100 µg/ml 4,6 Diamidino-2-phenylindole dihydrochloride (DAPI; a nucleic acid binding probe) was added from a solution in TES buffer. This was followed by incubation for 15 minutes at 37° C.

The sample was centrifuged down for 5 minutes @ 7500 rpm, and the supernatant was decanted off as waste (~450 µL). 500 µL of TES buffer was then added, and the sample was vortexed and centrifuged down at 5 minutes @ 7500 rpm. Again, the supernatant was decanted off by tapping as waste (~450 µL). A final 500 µL of TES wash buffer was added for final imaging, and 5 µL of the solution was placed on a slide with a long cover slip of glass. Phase contrast and fluorescence microscopy was conducted with the Leica DM5000 (Leica Microsystems, Buffalo Grove, Ill.).

The Texas Red label (ex 592, em 614 nm) was measured with a excitation band pass filter at 540-580 nm and emission band pass filter at 610-680 nm. The FITC label (ex 488, em 525 nm) was measured with an excitation band pass filter at 460-500 nm and an emission band pass filter at 512-543 nm. The DAPI probe (ex 355, em 460 nm) was measured with an excitation band pass filter at 340-380 nm and an emission band pass filter at 450-490 nm. The Cy5 label (ex 646, em 676 nm) was measured with an excitation band pass filter at 590-650 nm and an emission band pass filter at 665-735 nm.

The ideal multiplexing was demonstrated by combination of the rare earth nanoparticles with FITC, Texas Red, Cy5 and DAPI. The europium nanoparticle (ex 355, em 617 nm) was measured at an excitation filter band pass at 340-380 nm and emission long pass filter of >590 nm. Simultaneously measuring biomarkers for cancer cell type, metastatic potential and chemoresistance, along with a biomarker indicating the presence of cell nucleus was possible, along with the removal of false positives (i.e., white blood cells) by detecting the presence of the biomarker CD45. Current data allows for five signals. However, the assays/methods described and claimed herein have the potential for detection and measurement of six signals/biomarkers, if the rare earth nanoparticles can be multiplexed into three different emission signals. The europium label greatly increased signal over FITC and Texas Red by 2-3 orders of magnitude.

Example 4

Cell Response Assay for Prostate Cancer

Protease, like plasmin, is expressed during metastasis of malignant cells as part of the tissue regeneration and fibrinolysis process, indirectly promoting cell proliferation. Cancer cells use cell-bound plasmin to activate the plasminogen signaling for urokinase. Inhibitors of plasmin such as Bikunin and inhibitors of plasminogen activation such as PAI-1 prevent cell-bound plasmin activation and suppress tumor invasiveness.

A novel cell response assay for prostate cancer was developed by using PSA as a tissue type marker for prostate carcinoma (Biomarker A) that is always present in the disease state. The markers used in this example for metastatic potential (Biomarker B) were urokinase plasminogen activator (uPA) and plasminogen activator inhibitor (PAI-1), which is a measure of tissue invasiveness and is present in an aggressive cancer cell differentiation and growth with increased metastatic invasiveness potential. Chemo resistance nature (Biomarker C) was determined using PL2L piwi like antigen to determine the inhibitory response to tissue invasiveness.

The procedure shown in Example 3 was used to measure prostate cancer cells before and after treatment with and without camptothecin. Camptothecin is known to activate apoptosis in cancer cells and kill cancer cells like a chemotherapy agent (See Gupta, 1997). Cells were tested by the cell response assay and by a traditional prior art assay. The novel "cell response assay" utilized PSA as Biomarker A for cell type, the tumor invasiveness markers uPA & PAI-1 as Biomarker B for metastatic potential, and the cancer stem cell marker PL2L piwi like as Biomarker C for chemo resistance nature. The traditional assay used EpCAM as a marker for epithelial tissue type and cytokeratin (CK) as a marker of cells of cancer origin. Additionally, CD45, a marker for white blood cells, was used to reduce false results, with CD45 positive results being excluded from the analysis. Both the traditional and cell response assays used DAPI to determine the presence of cell nuclei.

The camptothecin concentration could be adjusted to be sufficient to kill >80%, 60% and 40% of the cancer cells in cultures. Cellular analysis showed cancer cell count to decrease as the cell death % increased and phosphatidylserine flopping increased. Cellular analysis showed biomarker B, namely uPA and PA1, to increase (or was detected in a greater number of cancer cells) when the cell death % was highest. Cellular analysis showed biomarker C, namely PL2L piwi like to decrease (or was detected in a lesser number of cancer cells) when the cell death % was highest. All three biomarkers co-exist in the disease state and were fundamental to progression or relapse of the disease. This analysis of the specific combination of biomarkers described and claimed herein allows the determination of the cellular response to treatments by simultaneously measuring cancer cell type, chemo resistance nature, and metastatic potential (with or without the additional measurement of cell viability), and is herein termed a "cell based response assay."

In contrast, in the traditional assay, the CD45 biomarker does not co-exist with EpCAM and CK. Both EpCAM and CK were present in all cells independent of the % of cells that were killed.

Example 5

The following procedure demonstrates the multiplexing of Biomarkers A, B and C as described herein previously to provide a general assay for all types of cancers. This procedure is performed as described herein above in Examples 1/3, except as follows: (a) the cancer suspension added to the procedure is selected from one of the following cell lines—SKBR, MCF or MDA (breast cancer), UC3 or T24 (bladder cancer), PC3-9 (prostate cancer), and A549 (lung cancer); and (b) the non-specific cancer cell biomarker cytokeratin is utilized for Biomarker A. In this particular example, antibodies to the cytokeratins 8/18/19 (wherein said antibodies are labeled with Cy5) are utilized as the first labeled probe that binds to Biomarker A. As described in Examples 1 and 3, antibodies to uPA or PAI-1 labeled with Texas Ted are utilized as the second labeled probe that binds to Biomarker B, and antibodies to PL2L piwi like labeled with FITC is utilized as the third labeled probe that binds to Biomarker C. The nucleic acid binding probe DAPI is also utilized as described in Examples 1 and 3.

This multiplexed assay utilizing a non-specific cancer cell biomarker allows the assays/methods described herein to be adapted for use with all types of cancers.

Thus, in accordance with the presently disclosed and/or claimed inventive concept(s), there has been provided a cell response assay, as well as methods of producing and using same, that fully satisfies the objectives and advantages set forth hereinabove. Although the presently disclosed and/or claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and/or claimed inventive concept(s).

REFERENCES

The following references, to the extent that they provide exemplary procedural or other details supplementary to those set forth herein, are specifically incorporated herein by reference in their entirety.

Alix-Panabieres et al. Full-length cytokeratin-19 is released by human tumor cells: a potential role in metastatic progression of breast cancer. Breast Cancer Research (2009) 11:R39.

Bobrow et al. Method for detection or quantitation of an analyte dependent enzyme activation system. U.S. Pat. No. 5,196,306, issued Mar. 23, 1993.

Carney et al. Assay for cancer monitoring based on levels of analyte components of the plasminogen activator system in body fluid samples U.S. Patent Application No. 2009/0286268, published Nov. 19, 2009.

Cheever et al. The prioritization of cancer antigens: A national cancer institute pilot project for the acceleration of translational research. Clin. Cancer Res. (2009) 15: 5323-5327.

Dyrssen. Rec. Tray. Chim. (1956) 75:748.

EP 0 515 194

Gao et al. PCT Publication No. WO 2008/048570, published Apr. 24, 2008.

Gao et al. Identification of Piwil2-Like (PL2L) Proteins that Promote Tumorigenesis. PLoSONE (2010) 5(10):e13406.

Goodman et al. Increased nanoparticle penetration in collagenase treated multicellular spheroids. International Journal of Nanomedicine (2007) 2(2):265-274.

Grady. System and method for cell analysis is microscopy. US Patent Publication No. 2008/0187198, published Aug. 7, 2008.

Gupta. Clin. Cancer. Res. (1997) 3:1653-1660.

Haar and Umland. Analyt. Chem. (1962) 191:81.

Harma et al. Europium Nanoparticles and Time-resolved Fluorescence for Ultrasensitive Detection of Prostate-specific Antigen. Clin. Chem. (2001) 47:561-8.

Herzenberg et al. The History and Future of the Fluorescence Activated Cell Sorter and Flow Cytometry: A View from Stanford. Clin. Chem. (2002) 48: 1819-27.

Horan et al. Fluorescent cell labeling for in vivo and in-vitro cell track. In Methods in Cell Biology, (1990) Vol 33, Chapter 42 Flow Cytometry. eds Darzynkiewicz and Crissman.

Kraus et al. Method and diagnostic agent for hemostasis diagnosis. U.S. Pat. No. 6,187,594, issued Feb. 13, 2001.

Krivacic et al. A rare cell detector for cancer. PNAS (2004) 101:10501-10504.

Lianidou and Markou. Clin. Chem. (2011) 57(9):1242-1255.

Matsumoto et al. Novel fine fluorescent particles. US Published Application No. 2007/0026407, published Feb. 1, 2007.

Mocellin et al. Circulating tumor cells: the 'leukemic phase' of solid cancers. TRENDS in Molecular Medicine (2006) 12(3):130-139.

Morikawa et al. Visualization of individual DNA molecules in solution by light microscopy: DAPI staining method. J. Biochem. (Tokyo) (1981) 89:693-6.

Pantel et al. Detection, clinical relevance and specific biological properties of disseminating tumour cells. Nature Reviews Cancer (2008) 8:329-340.

Pardal et al. Applying the principles of stem cell biology to cancer. Nature Reviews Cancer (2003) 3:895-902.

Patel et al. Clin. Chem. (2000), 46:1471-1477.

Punnoose et al. Molecular Biomarkers Analysis Using Circulating Tumor Cells. PLoS ONE (2010) 5:e12517.

Ryan et al. Phosphor combination and method particularly adapted for the use with explosives, for providing a distinctive information label. U.S. Pat. No. 3,772,099, issued Nov. 13, 1973.

Serigne. Chim. Phys. (1934) 31:47.

Shephard US atomic energy comm. Report AECU-3879

Smith et al. Detection of apoptotic cells using a synthetic fluorescent sensor for membrane surfaces that contain phosphatidylserine. Cell Death and Differentiation (2003) 10, 1357-1359.

Stary. J. Zhur. Neorg. Khim. (1959) 4:2412.

Ullman et al. Clin. Chem. (1996), 42:1518-1526.

Ulman et al. Luminescent oxygen channeling immunoassay. Proc. Natl. Acad. Sci. (1994) 91:5426-5430.

U.S. Pat. No. 5,834,196

U.S. Pat. No. 7,179,616

What is claimed is:

1. A method of monitoring cancer treatment in a cancer patient undergoing said treatment, wherein the treatment is monitored using a multiplexed direct affinity assay, and wherein the method comprises the steps of:

(A) isolating cells from a first biological sample taken from the cancer patient at a first time point;

(B) isolating cells from a second biological sample taken from the cancer patient at a second time point, wherein the cancer patient has been exposed to a cancer treatment between the first and second time points;

(C) reacting the isolated cells from the first biological sample with at least three affinity reagents for at least three biomarkers, wherein the isolated cells are reacted with the at least three affinity reagents in a single reaction, wherein each affinity reagent comprises a different fluorescent label whereby the different fluorescent labels are measured at different excitations and emissions wavelengths, and wherein the at least three biomarkers comprise:

(i) a cancer cell type biomarker;

(ii) a metastatic potential biomarker, wherein the metastatic potential biomarker is urokinase plasminogen activator (uPA) and/or plasminogen activator inhibitor (PAI-1); and (iii) a chemo resistance biomarker, wherein the chemo resistance biomarker is PL2L piwi like;

wherein biomarkers (i), (ii), and (iii) all co-exist in a cancer disease state, are fundamental to progression or relapse of the cancer disease state, and are all biochemically linked in a biochemical process; and wherein the presence of markers (ii) and (iii) are linked such that the presence of one facilitates absence of the other;

(D) reacting the isolated cells from the second biological sample with the at least three affinity reagents of (C), wherein the isolated cells are reacted with the at least three affinity reagents in a single reaction;

(E) simultaneously measuring, in a multiplexed assay, expression levels of the at least three biomarkers in the isolated cells from the first biological sample;

(F) simultaneously measuring, in a multiplexed assay, the expression levels of the at least three biomarkers in the isolated cells from the second biological sample;

(G) calculating a proportion of cells detected by the cancer cell type biomarker that are also detected by the metastatic potential biomarker in the first and second biological samples;

(H) calculating a proportion of cells detected by the cancer cell type biomarker that are also detected by the chemo resistance biomarker in the first and second biological samples; and
(I) administering a subsequent dose of the cancer treatment if:
  (1) the metastatic potential biomarker is present in a greater proportion of cancer cells detected by the cancer cell type biomarker in the second biological sample when compared to the first biological sample; and
  (2) the chemo resistance biomarker is present in a lesser proportion of cancer cells detected by the cancer cell type biomarker in the second biological sample when compared to the first biological sample.

2. The method of claim 1, wherein the cancer patient is suffering from a cancer selected from the group consisting of lung, bronchus, colon, rectum, pancreas, prostate, breast, liver, bile duct, bladder, ovary, brain, central nervous system (CNS), kidney, pelvis, uterine corpus, oral cavity, pharynx, melanoma, and combinations thereof.

3. The method of claim 1, wherein the at least one cancer cell type biomarker is selected from the group consisting of epithelial cell adhesion molecule (EpCAM), a cytokeratin, vimentin, galectin-3, a cadherin, an oncoprotein, an oncogene, and combinations thereof.

4. The method of claim 3, wherein the at least one cancer cell type biomarker comprises at least one of:
  (a) a combination of at least one type I cytokeratin and at least one type II cytokeratin;
  (b) a combination of vimentin and galectin-3;
  (c) a combination of N-cadherin and E-cadherin; and
  (d) an oncoprotein or oncogene selected from the group consisting of HER2/neu, VEGF-165, KRAS, EGFr, WAF, BAX-1, PDGF, Rb, Jagged 1, Notch, VEGF, VEGHR, k-Ras, CAIX, MIB1, MDM, PR, ER, SEL5, SEM1, PI3K, Akt2, twist 1, EML-4, ALK, Braf, DRAFF, c-met, and combinations thereof.

5. The method of claim 1, wherein at least one of the affinity reagents comprises a conjugate of a fluorescent label to an antibody to at least one of the biomarkers.

6. The method of claim 1, wherein each of the three fluorescent labels is selected from fluorescein-5-isothiocyanate (FITC), phycoerythrin, sulforhodamine 101(Texas Red), 2-[4-(aminoiminomethyl)phenyl]-1H-Indole-6-carboximidamide (DAPI), 3H-Indolium (Cy5), 1H-benz[e]indolium (Cy 5.5), 3H-Indolium (Cy 7), rare earth metals, rare earth element-containing nanoparticles, and combinations and derivatives thereof.

7. The method of claim 1, wherein the biological sample is further defined as a tissue sample.

8. The method of claim 1, wherein the method is further defined as a method of monitoring breast cancer treatment, and wherein biomarker (i) is HER2/neu.

9. The method of claim 1, wherein the method is further defined as a method of monitoring prostate cancer treatment, and wherein biomarker (i) is PSA.

* * * * *